United States Patent [19]

Yoshida

[11] Patent Number: 4,509,076
[45] Date of Patent: Apr. 2, 1985

[54] DEFECT INSPECTION APPARATUS

[75] Inventor: Hajime Yoshida, Tokyo, Japan

[73] Assignee: Hajime Industries Ltd., Tokyo, Japan

[21] Appl. No.: 617,237

[22] Filed: Jun. 5, 1984

Related U.S. Application Data

[63] Continuation of Ser. No. 409,032, Aug. 17, 1982, abandoned, which is a continuation of Ser. No. 131,543, Mar. 18, 1980, abandoned.

[30] Foreign Application Priority Data

Mar. 22, 1979 [JP] Japan .................................. 54-33406

[51] Int. Cl.³ .............................................. H04N 7/18
[52] U.S. Cl. ..................................... 358/106; 250/563; 356/431
[58] Field of Search ................ 358/106; 250/562, 563, 250/572; 356/237, 430, 431

[56] References Cited

U.S. PATENT DOCUMENTS

| | | | |
|---|---|---|---|
| 3,646,353 | 2/1972 | Bhullar et al. | 356/431 |
| 3,715,476 | 2/1973 | Watanabe | 358/106 |
| 3,795,452 | 3/1974 | Bourdelais et al. | 356/431 |
| 4,011,457 | 3/1977 | Wolf | 356/431 |
| 4,110,048 | 8/1978 | Akutsu et al. | 250/563 |

Primary Examiner—Joseph A. Orsino, Jr.
Attorney, Agent, or Firm—Murray Schaffer

[57] ABSTRACT

A defect inspection apparatus having a television camera which picks up an object to be inspected and produces a video signal for inspecting defects on the object, wherein the apparatus comprises a detection section which outputs a signal responding to the positive changes of the video signal with respect to time and a further detection section which outputs a signal in response to the negative changes of the video signal with respect to time, so that a defect detection signal is only output when, after one of the detection sections generates an output, the other detection section generates an output within a given time period.

2 Claims, 20 Drawing Figures

DEFECT INSPECTION APPARATUS

This is a continuation of U.S. Ser. No. 409,032, filed 8/17/82, now abandoned, which is a continuation of Ser. No. 131,543, filed 3/18/80, now abandoned.

BACKGROUND OF THE INVENTION

1. Field of the Invention

The present invention is related to a defect inspection apparatus which inspects the defects such as flaws on objects of industrial products or the like.

2. Description of the Prior Art

Conventionally, the inspection of defects such as flaws on objects of industrial products or the like, for instance, the industrial products which flow through on a belt conveyor or the like, is conducted by human visual sight. The defect inspection under the conventional methods contain many faults such as skill is required, so that the conventional method is inadequate for automatic product inspection, etc. Further, the inspection dependent upon the human visual sight contained problems of accuracy.

OBJECTS AND SUMMARY OF THE INVENTION

Therefore, the main purpose of the present invention is to provide a novel defect inspection apparatus free of the above mentioned conventional faults.

Another object of the invention is to provide a defect inspection apparatus which can accurately and automatically conduct the inspection of small defects such as flaws or the like on objects.

According to an aspect of the present invention defect inspection apparatus is provided which comprises:
 (a) image sensing means for picking up an object to be inspected and producing a video signal of said object;
 (b) a first detection section for receiving the video signal and producing an output in response to a positive changing ratio of the video signal with respect to time;
 (c) a second detection section for receiving the video signal and producing an output in response to a negative changing ratio of the video signal with respect to time; and
 (d) output means for producing a defect detection signal only after one of said first and second detection sections produces an output, the other produces an output within a given period.

The other objects, features and advantages of the present invention will become apparent from the following description taken in conjunction with the accompanying drawings.

BRIEF DESCRIPTION OF THE DRAWINGS

FIGS. 3A through 3I and FIGS. 4A through 4I are waveform diagrams illustrated in order to explain the operation of the example shown on FIG. 1.

DESCRIPTION OF THE PREFERRED EMBODIMENT

Figure 1:
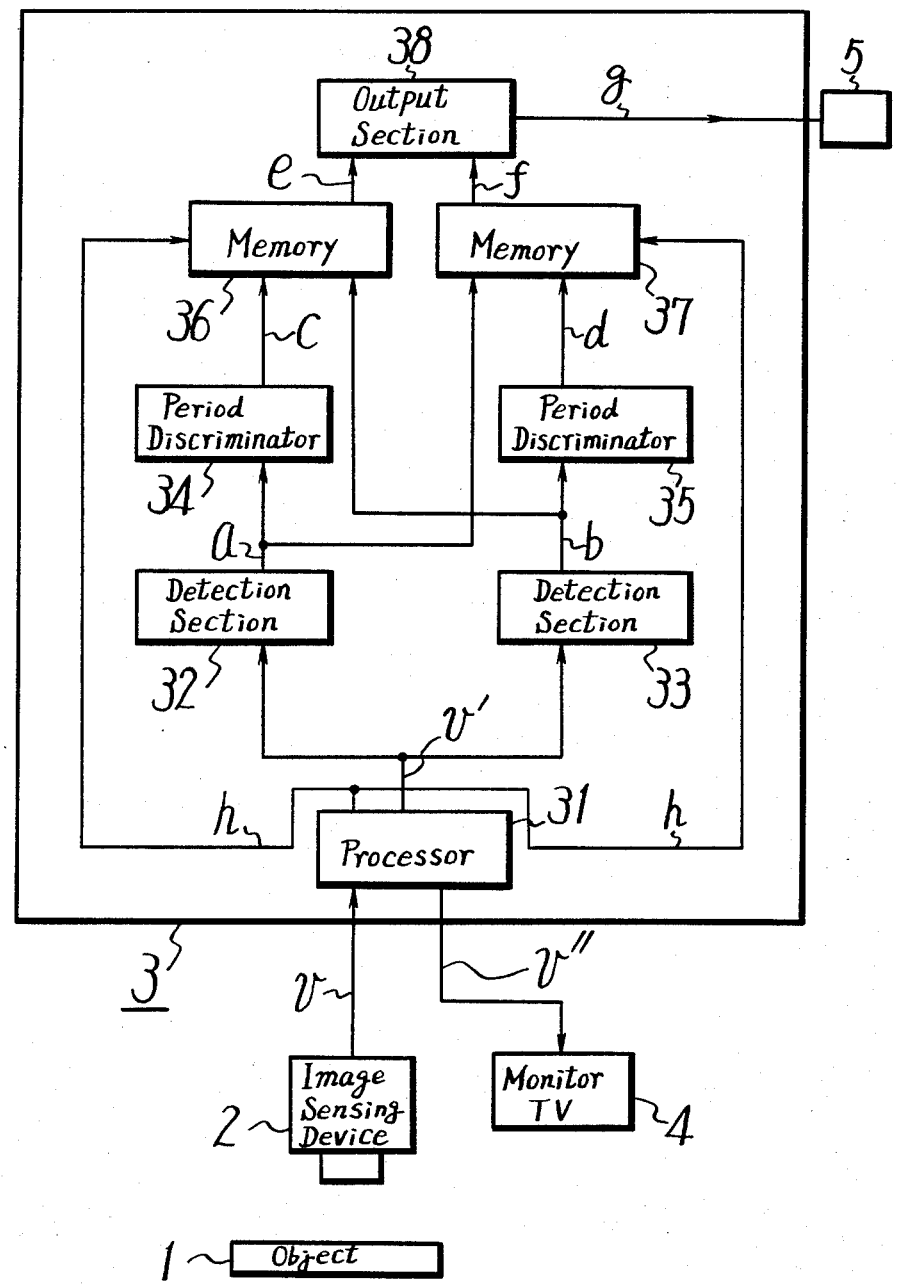
FIG. 1 shows a systematic block diagram showing an example of the defect inspection apparatus according to the present invention.

An example of the defect inspection apparatus under the present invention will be explained in reference with the drawings hereunder. FIG. 1 illustrates a systematic block diagram of an example of the defect inspection apparatus under the present invention. On the same drawing, 1 designates an object to be inspected such as an industrial product or the like; 2 an image sensing device such as a black and white television camera which outputs a video or image signal v by picking up the inspected object 1; 3 an object inspection apparatus in general which processes the image signal v from television camera 2; and 4 a monitor television receiver which reproduces the image signal of the inspected object 1 by receiving the image signal v" from the object inspection apparatus 3.

The object inspection apparatus 3 under the present invention is constructed by a processor 31 for the video signal v such as a video amplifier and horizontal synchronizing separator, a 1st detection section 32, for example, differentiation circuit, a 2nd detection section 33, for example, differentiation circuit, a 1st period discriminator 34, for example, one-shot multivibrator or timer, a 2nd period discriminator 35, for example, one-shot mutivibrator or timer, a 1st memory 36 such as flip-flop, a 2nd memory 37 such as flip-flop, and an output section 38, for example, OR-gate.

Processor 31 has functions such as to receive the image signal v corresponding to the inspected object 1 from television camera 2, to amplify the same and process the same by deleting the unnecessary components, to make image signal v', which is respectively sent to the 1st detection section 32 and the 2nd detection section 33, to process the image signal v from television camera 2 and send an image signal v" to monitor television receiver 4, and further to receive the image signal v from television camera 2, and make, for instance, horizontal synchronizing signal h (refer to FIGS. 3I and 4I) and supply such signal h to the 1st memory 36 and the 2nd memory 37 respectively.

At the 1st detection section 32, when the changing ratio of the supplied image signal v' with respect to time is, for instance, higher than a positive given value, a signal a is output and then fed to the 1st period discriminator 34 and the 2nd memory 37. On the other hand, at the 2nd detection section 33, when the changing ratio of the supplied image signal v' with respect to time is, for instance, over a negative given value, a signal b is output and then fed to the 2nd period discriminator 35 as well as the 1st memory section 36. The 1st period discriminator 34 receives a signal a from the 1st detection section 32, then outputs a signal c for a given period and sends the same to the 1st memory 36. Further, the 2nd period discriminator 35 receives the signal b from the 2nd detection section 33, then outputs a signal d for a given period and sends the same to the 2nd memory 37. The 1st memory 36 outputs a signal e and sends the same to the output sections 38 when there are signal c from the 1st period discriminator 34 and also the signal b from the 2nd detection section 33. The 2nd memory 37 outputs a signal f and supplies the same to the output section 38 when there are the signal d from the 2nd period discriminator 35 and also the signal a from the 1st detection section 32. Output section 38 outputs a defect detection signal g when either of signals e or f is received or when both of signals e and f are received.

Further, the 1st memory 36 as well as the 2nd memory 37 are both cleared by the horizontal synchronizing signal h from the processor section 31.

The operation of the defect inspection apparatus under the present invention with the above mentioned construction is described as follows. It is noted that the present invention will be explained with an example case where a defect such as a black dot or the like is inspected on a middle seal of a bottle cap whereas the middle seal is a white coloured disc shape as the inspected object 1.

Figure 2:
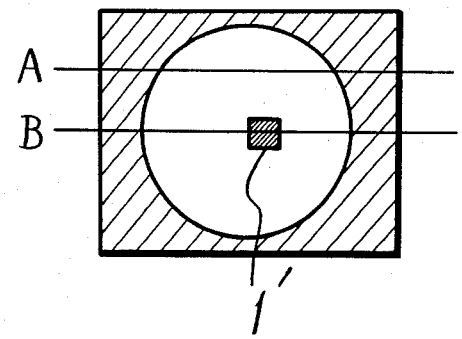
FIG. 2 shows a front view of the screen of a monitor television receiver.
Figure 2:
Figure 2:
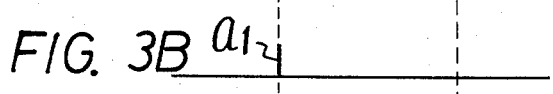
Figure 2:
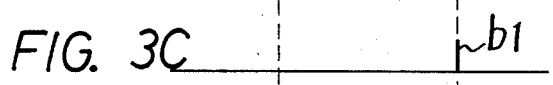
Figure 2:
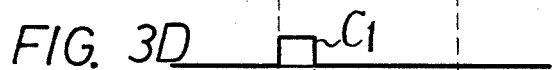
Figure 2:
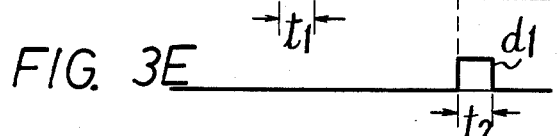
Figure 2:
Figure 2:
Figure 2:
Figure 2:
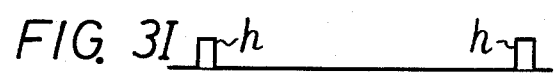
Figure 2:
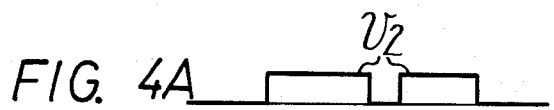
Figure 2:
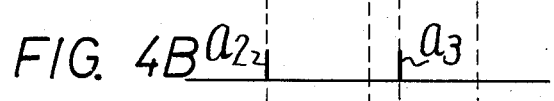
Figure 2:
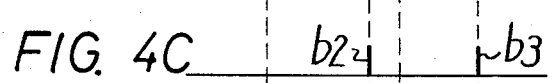
Figure 2:
Figure 2:
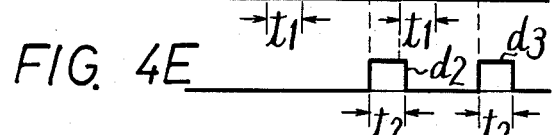
Figure 2:
Figure 2:
Figure 2:
Figure 2:
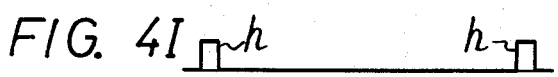

FIG. 2 is the front view of the screen of the monitor television receiver 4 on which the image of an object, for instance, a middle seal 1 in a black background with a black dot 1' is reproduced by the video camera 2. Image signals for one horizontal portion of television camera 2 as shown with straight lines A and B on FIG. 2, for instance, appear as such waveforms as v1 and v2 on FIGS. 3A and 4A respectively. When image signals such as v1 and v2 as shown on FIG. 3A and FIG. 4A as an example, are received at the 1st detection section 32, pulse signals a1, a2 and a3 are respectively output from the 1st detection section 32 at the rising-up edges of the image signals v1 and v2 as shown on FIGS. 3B and 4B. On the other hand, at the 2nd detection section 33, when image signals such as v1 and v2 as shown on FIG. 3A and FIG. 4A are received, pulse signals b1, b2 and b3 are respectively output from the 2nd detection section 33 at the falling-down edges of image signals v1 and v3 as shown on FIG. 3C and 4C. The 1st period discrimination section 34 receives pulse signals a1, a2 and a3 as shown on FIG. 3B and FIG. 4B from the 1st detection section 32, and outputs pulse signals c1, c2 and c3 respectively each with a given pulse width t1 at the rising-up edges of pulse signals a1, a2 and a3 as shown on FIG. 3D and FIG. 4D. Also, the 2nd period discriminator 35 receives the pulse signals b1, b2 and b3 as shown on FIGS. 3C and 4C from the 2nd detection section 33, and outputs pulse signals d1, d2 and d3 respectively each with a given pulse width t2 at the rising-up edges of pulse signal b1, b2 and b3 as shown on FIG. 3E and FIG. 4E respectively. In this case, the periods or the pulse widths t1 and t2 of the pulse signals c1, c2, c3, d1, d2 and d3 are respectively established in conjunction with the size of the defect 1' that must be detected.

Firstly, in the case of the scan line A on FIG. 2, as shown on FIG. 3 and FIG. 4, the 1st memory 36 does not receive pulse signal b1 from the 2nd detection section 33 during the period t1 of pulse signal c1 from the 1st period discriminator section 34, and as well, the 2nd memory 37 does not receive signal a1 from the 1st detection section 34 during the period t2 of signal d1 from the 2nd period discriminator section 35. Therefore, for the portion corresponding to scan line A of FIG. 2, the 1st memory 36 and the 2nd memory 37 both do not output signals e and f as shown on FIG. 3F and FIG. 4G. On the other hand, in the case of scan line B on FIG. 2, the 1st memory 36 does not receive signals b2 and b3 from the 2nd detection circuit 33 during the period t1 of signals c2 and c3 from the 1st period discriminator section 34. Accordingly, for the portion corresponding to the scan line B of FIG. 2, the 1st memory 36 does not output signal e as shown on FIG. 4F. However, the 2nd memory 37 receives pulse signal a3 from the 1st detection section 32 during the period t2 of the signal d2 from the 2nd period discriminator section 35, so that in this case, the 2nd memory 37 outputs pulse signal f as shown on FIG. 4G. Therefore, if the output section 38 is so arranged that output signal g is output therefrom when output signal f from the 2nd memory 37 is received by the output section 38, as described above, when the 2nd memory 37 outputs signal f, the output section 38 outputs a defect detection signal g. In other words, when there is defect 1' on the inspected object 1 only, the output section 38 outputs defect detection signal g. This output signal g is supplied to, for instance, an indicator section 5 which is a buzzer or a lamp or the like to indicate the existence of defects.

The above explanation is given on the case where a white based inspected object exists on a black background, where a defect such as a black dot is to be detectd within the white base, but in the reverse, a black inspected object may be placed on a white background, and a white defect may be detected within the black base, whereas the output section 38 may be arranged to output a defect detection signal g when the output signal e from the 1st memory 36 is received by the output section 38.

Further, in the case that the colour of the inspected object, colour of the background, colour of the defect and so forth are different to the black or white as above mentioned, by picking up each colour by the television camera, image signals with black and white levels responding to the respective colours may be obtained and hence for such cases also the present invention may be obviously applied with the same effects.

As described above, under the present invention, defects on an inspected object may be surely and automatically inspected and the advantages provided to such fields of applications is enormous.

The above description is given on a single preferred embodiment of the present invention, but it will be apparent that many modifications and variations could be effected by one skilled in the art without departing from the spirits or scope of the novel concepts of the invention. Therefore, the spirits or scope of the invention should be determined by the appended claims only.

I claim as my invention:

1. A defect inspection apparatus for inspecting small defects such as flaws comprising:
    (a) image sensing means for picking up an object to be inspected and producing an analog video signal of said object;
    (b) processor means for receiving said analog video signal and separating therefrom a horizontal synchronizing signal component and a video signal free of any unnecessary component;
    (c) a first section for receiving said video signal and converting said video signal to a digital signal having an output differentiation pulse at a rising edge thereof;
    (d) a second detection section for receiving said video signal and converting said video signal to a digital signal having an output differentiation pulse at a falling edge thereof;
    (e) a first period discriminator for receiving the output pulse from said first detection section and producing a signal with a period which is established in conjunction with the size of a defect to be detected;
    (f) a second period discriminator for receiving the output pulse from said second detection section and producing a signal with a period the same as that of the signal from said first period discriminator;

(g) a first memory for receiving the signals from said first period discriminator section and the output pulse from second detection section and producing a signal when both of said signals are present so as to detect a defect of a size smaller than that determined by the signal with the period derived from said first period discriminator, said horizontal synchronizing signal component being supplied to said first memory after receipt of the signals from said first period discriminator section and the output pulse from said second detection section so as to constantly clear said memory;

(h) a second memory for receiving the signals from said second period discriminator section and the output pulse from said first detection section and producing a signal when both of said signals are present so as to detect the defect of a size smaller than that determined by the signal with the period derived from said second period discriminator, and said horizontal synchronizing signal component being supplied to said second memory after receipt of the signals from said second period discriminator section and the output pulse from said first detection section so as to constantly clear said memory;

(i) output means responsive to said first and second memories for producing a defect detection signal when either one or both of said first and second memories produce output signals.

2. The defect inspection apparatus as claimed in claim 1 wherein said means for separating a horizontal synchronizing signal from the video signal provides a horizontal synchronizing signal component to said first and second memories to clear them.

* * * * *

UNITED STATES PATENT AND TRADEMARK OFFICE
CERTIFICATE OF CORRECTION

PATENT NO. : 4,509,076
DATED : April 2, 1985
INVENTOR(S) : Hajime Yoshida

It is certified that error appears in the above-identified patent and that said Letters Patent are hereby corrected as shown below:

On the title page;

[30] Foreign Application Priority Data

March 22, 1979 (JP) Japan        54-33460

Signed and Sealed this

Thirteenth  Day of  August 1985

[SEAL]

*Attest:*

DONALD J. QUIGG

*Attesting Officer*    *Acting Commissioner of Patents and Trademarks*